United States Patent
Mahendar et al.

(10) Patent No.: US 9,249,139 B2
(45) Date of Patent: Feb. 2, 2016

(54) INDOLIZINONE BASED DERIVATIVES AS POTENTIAL PHOSPHODIESTERASE 3 (PDE3) INHIBITORS AND A PROCESS FOR THE PREPARATION THEREOF

(71) Applicant: COUNCIL OF SCIENTIFIC & INDUSTRIAL RESEARCH, New Delhi (IN)

(72) Inventors: Budde Mahendar, Hyderabad (IN); Saidulu Mattapally, Hyderabad (IN); Mettu Ravinder, Hyderabad (IN); Sanjay Kumar Banerjee, Hyderabad (IN); Vaidya Jayathirtha Rao, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/168,370

(22) Filed: Jan. 30, 2014

(65) Prior Publication Data

US 2014/0296530 A1    Oct. 2, 2014

(30) Foreign Application Priority Data

Feb. 1, 2013    (IN) .............................. 287/DEL/2013

(51) Int. Cl.
*C07D 221/02* (2006.01)
*C07D 471/04* (2006.01)

(52) U.S. Cl.
CPC .................................... *C07D 471/04* (2013.01)

(58) Field of Classification Search
CPC .................................................... C07D 471/04
USPC ....................................................... 546/183
See application file for complete search history.

(56) References Cited

PUBLICATIONS

Dannhardt et al. European Journal of Medicinal Chemistry (1987), 22(6), 505-10.*

* cited by examiner

*Primary Examiner* — Nizal Chandrakumar
(74) *Attorney, Agent, or Firm* — Abelman, Frayne & Schwab

(57) ABSTRACT

The present invention provides compounds of general formula A useful as potential phosphodiesterase3 (PDE3) inhibitory agents and a process for the preparation thereof. The derivatives of formula A can be employed as therapeutics in human and veterinary medicine, where they can be used, for example, for the treatment and prophylaxis of the following diseases: heart failure, dilated cardiomyopathy, platelet inhibitors, cancer and obstructive pulmonary diseases.

Formula 1

Where in Z = COOMe, COOEt
R = substituted phenyl
R =

A = H, alkyl, alkoxy, halo, dihalo
B = H, alkyl, alkoxy, halo, dihalo
C = H, alkyl, alkoxy, halo, dihalo

3 Claims, 2 Drawing Sheets

Scheme -1

Z = electron withdrawing group
R = H, alkyl, alkoxy, halo, dihalo

Scheme -2

Z = electron withdrawing group
R = H, alkyl, alkoxy, halo, dihalo

INDOLIZINONE BASED DERIVATIVES AS POTENTIAL PHOSPHODIESTERASE 3 (PDE3) INHIBITORS AND A PROCESS FOR THE PREPARATION THEREOF

FIELD OF THE INVENTION

The present invention relates to novel indolizinone based derivatives as potential phosphodiesterase3 (PDE3) inhibitors and process for the preparation thereof. Particularly, the present invention relates to indolizinone based derivatives of formula 1 and process for preparing of said compounds.

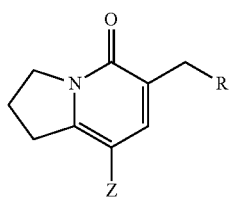

Formula 1

Where in Z = COOMe, COOEt
R = substituted phenyl

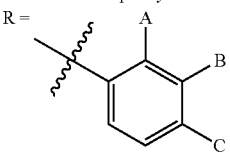

R =

A = H, alkyl, alkoxy, halo, dihalo
B = H, alkyl, alkoxy, halo, dihalo
C = H, alkyl, alkoxy, halo, dihalo More particularly, the present invention relates to indolizinone based derivatives useful as phosphodiesterase 3 (PDE3) inhibitory agents. The structural formula of these indolizinone based derivatives is given below.

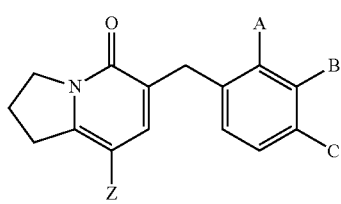

1a-p

BACKGROUND OF THE INVENTION

Congestive heart failure (CHF) is a major cause of death in patients with heart disease. Digitalis glycosides (Drug that is extracted from the leaves of the foxglove plant) have been used for the treatment of CHF for more than 200 years (Gheorghiade, M.; Zarowitz, B. J.; *Am. J. Cardiol.*, 1992, 69, 48G). However, application of these agents are limited because of their narrow therapeutic window and their propensity that cause life-threatening arrhythmias (arrhythmogenic liability). Thus digitalis has been replaced by a new class of cardiotonic agents named as a well known PDE3 inhibitor Amrinone and Milrinone, a 2-oxopyridine derivative that has been introduced to the clinic for the treatment of CHF in place of digitalis (Kikura, M.; Levy, J. H.; *Int. Anestesiol. Clin.*, 1995, 33, 21). These PDE inhibitors display a greater safety profile and improved efficacy on patient survival.

Phosphodiesterases are a class of intracellular enzymes responsible for the hydrolysis of cyclic adenosine monophosphate (c-AMP) and cyclic guanosine monophosphate (c-GMP) which are involved in the regulation of important cell functions, such as secretion, contraction, metabolism, and growth (Potter, B. V. L.; Transmembrane Signalling Second Messenger Analogues and Inositol Phosphates. In Comprehensive Medical Chemistry; Hansch, C.; Sammes, P. G.; Taylor, J. B.; Eds. Pergamon Press: Oxford, 1990; pp 102-128). On the basis of structure, and substrate specificity PDE enzymes can be grouped into eleven different families, PDE1 to PDE11 (Beavo, J. A.; *Physiol. Rev.*, 1995, 75, 725).

Each PDE isozyme has a conserved C-terminal catalytic domain and unique N-terminal regulatory domain. These isozymes are found in different tissues and cells of the humans such as smooth muscle, brain, heart, lung, platelets, lymphocytes etc. and in other species (Bender, A. T.; Beavo, J. A.; *Pharmacol Rev.*, 2006, 58, 488). PDE3 and PDE4 are well established in cardiovascular tissues (Nicholson, C. D.; Challiss, R. A. J.; Shahid, M.; *Trends Phahrmacol Sci.*, 1991, 12, 19). Among all subtypes of PDE, PDE3 is predominantly expressed in heart and platelets. Thus PDE3 play an important role in heart and platelet (Palson, J. B.; Strada, S. J.; *Annu. Rev. Pharmacol. Toxicol.*, 1996, 36, 403).

Inhibition of PDE brings about various physiological reactions, for example inhibition of PDE3 enhances myocardial contraction, produces vasodilatation, and suppresses platelet aggregation (Abadi, A. H.; Ibrahim, T. M.; Abouzid, K. M.; Lehmann, J.; Tinsley, H. N.; Gary, B. D.; Piazza, G. A.; *Bioorg. Med. Chem.* 2009, 17, 5974). These are the reasons why PDE3 inhibitors can be used to treat heart failure.

In addition, the PDE3 isozyme is specific for c-AMP and has no effect on c-GMP and calmodulin. Therefore, inhibition of PDE3 isoenzyme in cardiovascular tissues may lead to high levels of c-AMP and consequent inotropic effect.

Recent studies revealing that PDE3, PDE4, and PDE5 isozymes are over expressed in cancerous cells compared with normal cells. Thus inhibition of PDE3 together with other PDE's may lead to inhibition of tumor cell growth and angiogenesis (Cheng J. B.; Grande, J. P.; *Exp. Biol. Med.*, 2007, 232, 38).

Recently, PDE3/4 inhibitors have attracted considerable interest as potential therapeutic agents for diseases including chronic obstructive pulmonary disease (COPD). PDE4 or PDE3 inhibitors alone are unable to inhibit spasmogen-induced contraction of human airway, but in combination act synergistically. While PDE3 inhibitor has been shown to inhibit cough, PDE4 inhibitor may be able to stimulate mucociliary clearance. This diverse spectrum of biological effects has thus implicated PDE3/4 inhibitors as potential therapeutic agents for a range of disease indications including COPD. (Banner, K. H.; Press, N. J.; *Br. J. Pharmacol.*, 2009, 157(6): 892-906.)

The present invention describes the synthesis of novel indolizinone based derivatives as inhibitors of phosphodiesterase3 (PDE3). PDE3 inhibitors are useful for the prevention of heart failure and inhibit platelet aggregation.

The following references are examples for the synthesis and biological evaluation of some of the PDE or PDE3 inhibitors. The prior art contain useful information and discussion on the preparation and properties of PDE inhibitors.

U.S. Pat. No. 4,963,561, reported synthesis of novel 1,3-dihydro-2H-imidazo[4,5-b]pyridin-2-ones having an aryl or heteroaryl group on the $6^{th}$ position, useful as phosphodiesterase inhibitors, prepared by reacting a 2-amino-5-(aryl or heteroaryl)pyridine-3-carboxylic acid with diphenylphosphoryl azide.

US Pat. No. 20070208051, reports PDE3/4 inhibition by novel N-(alkoxyalkyl) carbamoyl substituted 6-phenyl-benzonaphthyridine derivatives.

Recently our publication reported [Ravinder et al *Bioorg. Med. Chem. Lett.*, (2012)] Synthesis and Evaluation of Novel 2-Pyridone Derivatives as Inhibitors of Phospho-diestarase3 (PDE3): A Target for Heart Failure and Platelet Aggregation.

Wang et al., *Bioorg Med Chem Lett.*, (2012 Feb. 9) reports synthesis and evaluation of Sildenafil analogs against human phosphodiesterase5 (PDE5).

FIG. 1

Amrinone    Milrinone

Phosphodiesterase3 (PDE3) inhibitors

OBJECTIVES OF THE INVENTION

The main objective of the present invention is to provide novel indolizinone based analogues useful as potential phosphodiesterase 3 (PDE3) inhibitors. Yet another object of this invention is to provide a process for the preparation of novel indolizinone based derivatives.

SUMMARY OF THE INVENTION

The present invention is directed towards the synthesis of compound of formula 1 having phosphodiesterase 3 (PDE3) inhibition activity.

Formula 1

Where in
Z = COOMe, COOEt
R = substituted phenyl

R =

A = H, alkyl, alkoxy, halo, dihalo
B = H, alkyl, alkoxy, halo, dihalo
C = H, alkyl, alkoxy, halo, hihalo In an embodiment of the present invention, the novel indolizinone based analogues are represented by the following compounds of formula 1a-p.

1a-p

In another embodiment of the invention, the halogen is selected from the group consisting of fluorine, chlorine and bromine.

In yet another embodiment the indolizinone (1a-p) based analogues are represented as:

Ethyl 6-benzyl-5-oxo-1,2,3,5-tetrahydroindolizinone-8-carboxylate (1a)

Ethyl 6-(2-fluorobenzyl)-5-oxo-1,2,3,5-tetrahydroindolizinone-8-carboxylate (1b)

Ethyl 6-(3-fluorobenzyl)-5-oxo-1,2,3,5-tetrahydroindolizinone-8-carboxylate (1c)

Ethyl 6-(4-fluorobenzyl)-5-oxo-1,2,3,5-tetrahydroindolizinone-8-carboxylate (1d)

Ethyl 6-(2-chlorobenzyl)-5-oxo-1,2,3,5-tetrahydroindolizinone-8-carboxylate (1e)

Ethyl 6-(3-chlorobenzyl)-5-oxo-1,2,3,5-tetrahydroindolizinone-8-carboxylate (1f)

Ethyl 6-(4-chlorobenzyl)-5-oxo-1,2,3,5-tetrahydroindolizinone-8-carboxylate (1g)

Ethyl 6-(2,4-dichlorobenzyl)-5-oxo-1,2,3,5-tetrahydroindolizinone-8-carboxylate (1h)

Ethyl 6-(2-bromobenzyl)-5-oxo-1,2,3,5-tetrahydroindolizinone-8-carboxylate (1i)

Ethyl 6-(3-bromobenzyl)-5-oxo-1,2,3,5-tetrahydroindolizinone-8-carboxylate (1j)

Ethyl 6-(4-bromobenzyl)-5-oxo-1,2,3,5-tetrahydroindolizinone-8-carboxylate (1k)

Ethyl 5-oxo-6-(2-(trifluoromethyl)benzyl)-1,2,3,5-tetrahydroindolizinone-8-carboxylate (1l)

Ethyl 5-oxo-6-(4-(trifluoromethyl)benzyl)-1,2,3,5-tetrahydroindolizinone-8-carboxylate (1m)

Ethyl 6-(4-methylbenzyl)-5-oxo-1,2,3,5-tetrahydroindolizinone-8-carboxylate (1n)

Ethyl 6-(4-ethylbenzyl)-5-oxo-1,2,3,5-tetrahydroindolizinone-8-carboxylate (1o)

Ethyl 6-(4-isopropylbenzyl)-5-oxo-1,2,3,5-tetrahydroindolizinone-8-carboxylate (1p)

The present invention further provides a process for preparation of novel indolizinones based analogues of formula 1, and said process comprising of following steps:

1. reacting an olefin of formula 3

3 with a substituted benzaldehydes of formula 2

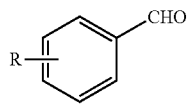

in presence of a catalyst and isolating the compound of formula 4

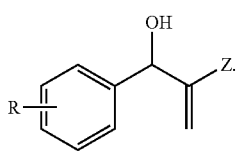

2. adding pyridine to a compound of formula 4 of step 1 in presence of an organic solvent, and under inert atmosphere followed by addition of an acetyl chloride and isolating the acetylated compound of formula 5

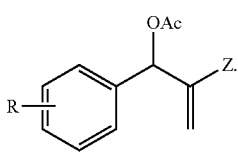

3. reacting an acetylated compounds of formula 5 of step 2 with substituted 2-pyrolidine-2-ylidene acetate of formula 6 in presence of an organic solvent and a base and isolating the compound of formula 1

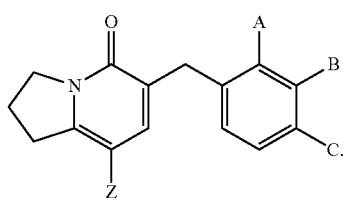

The present invention further provides a process for preparation of novel indolizinones based analogues of formula 1a-p, and said process comprising of following steps
1. reacting an olefin of formula (3a) with a substituted benzaldehydes of formula (2a-p) in presence of a catalyst and isolating the compound of formula. 4a-p
2. adding pyridine to a compound of formula 4 a-p of step 1 in presence of an organic solvent, under argon atmosphere followed by addition of an acetyl chloride and isolating the acetylated compound of formula 5 a-p.
3. reacting acetylated compounds of formula 5 a-p of step 2 with a substituted 2-pyrolidine-2-ylidene acetate of formula 6a in presence of an organic solvent and a base and isolating the compound of formula 1a-p.

In yet another embodiment of the present invention the catalyst is selected from the group consisting of quinuclidine 3-HQD (3-hydroxy quinuclidine), 3-quinuclidone, DBU, pyrrocoline, DMAP (dimethylaminopyridine), TMPDA (N,N,N$^1$,N$^1$-tetramethyl-1,3-propanediamine), imidazole, TMG (tetramethyl guanidine), triethyl amine, dimethyl sulfide/TiCl$_4$, TiCl$_4$, trialkylphosphines and RhH(PPh$_3$)$_4$, In yet another embodiment of the present invention the reaction between the substituted aromatic aldehyde of formula 2 and an olefin of formula 3 is carried out at a temperature ranging between 25-35° C.

In another embodiment of the present invention the reaction between the pyridine and a compound of formula 4 in presence of an organic solvent is carried out for a time period ranging between 1-2 hour and the reaction between the acetyl chloride with the above said solution is carried out at a temperature ranging between 25-35° C.

In another embodiment of the present invention the reaction between the 2-pyrolidne-2-ylidene acetate of formula 6 and a compound of formula 5 is carried out for a time period ranging between 4-5 hour.

In another embodiment of the present invention the base is selected from the group consisting of NaH(100%), NaH (60%), NaOMe, NaOEt and t-BuOK.

In another embodiment of the reaction the organic solvents used is selected from the group consisting of tetrahydrofuran, acetonitrile and dimethylformamide.

In another embodiment of the reaction the compound of formula 4 is selected from the group consisting of ethyl 2-(hydroxyl(phenyl)methyl)acrylate, ethyl 2-((fluorophenyl)(hydroxyl)methyl)acrylate, ethyl 2-((3-fluorophenyl)hydroxyl) methyl)acrylate, ethyl-2-((4-fluorophenyl)(hydroxul) methyl)acrylate, ethyl 2-((2-chlorophenyl)hydroxyl)methyl) acrylate, ethyl 2-((3-chlorophenyl)(hydroxyl)methyl) acrylate, ethyl 2-((4-chlorophenyl)(hydroxyl)methyl) acrylate, ethyl 2((2,4-dichlorophenyl)hydroxyl)methyl) acrylate, ethyl 2-((bromophenyl)(hydroxyl)methyl)acrylate, ethyl-2-(hydroxyl(2-(trifluoromethyl)phenyl)methyl)acrylate, and ethyl-2(hydroxyl(4(trifluoromethyl)phenyl)methyl) acrylate, ethyl 2-(hydroxyl(p-tolyl)methyl)acrylate.

In another embodiment of the reaction, the compound of formula 5 is selected from the group consisting of ethyl 2-(acetoxy(phenyl)methyl)acrylate, ethyl 2-(acetoxy(2-fluorophenyl)methyl)methyl)acrylate, ethyl 2-(acetoxy(3-fluorophenyl)methyl)acrylate and ethyl2-(acetoxy(2-fluorophenyl)methyl)acrylate.

In another embodiment of the reaction the aromatic aldehyde is selected from the group consisting of alkyl, hydroxyl, halo, dihalo and hydrogen substituted aromatic aldehyde.

In another embodiment of the reaction, the compounds of formula 1 are used as Phosphodiesterase 3 (PDE3) inhibitory agents.

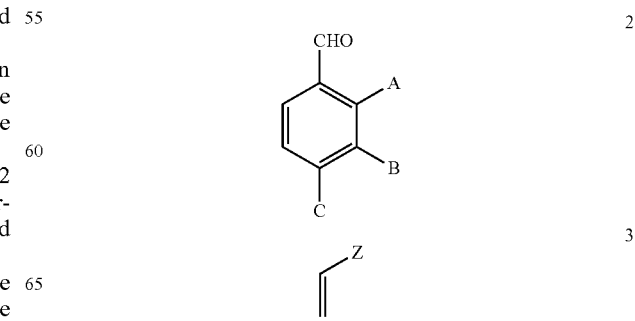

-continued

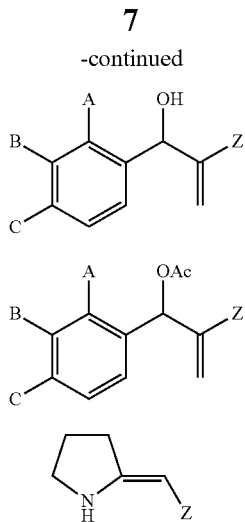

where in A = H, B = H, C = H
A = F, Cl, Br, CF₃, B = H, C = H
B = F, Cl, Br, A = H, C = H
A = H, B = H, C = F, Cl, Br, CF₃, Me, Et, iPr, OMe
A = Cl, C = Cl, B = H
Z = electron withdrawing group wherein Z=electron withdrawing group

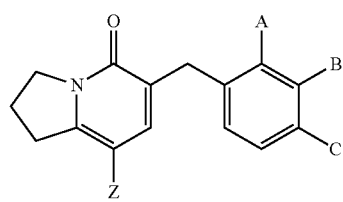

1a-p

DETAILED DESCRIPTION OF THE INVENTION

Figure 1:
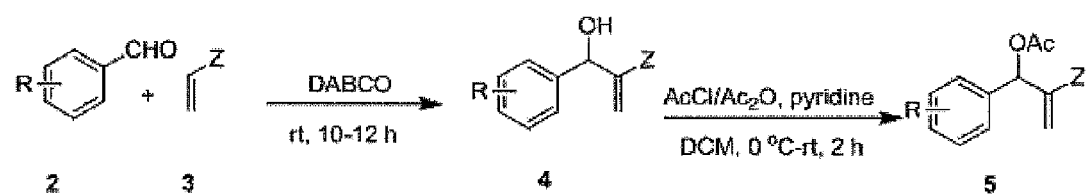
FIG. 1—Scheme 1 illustrates the process for preparation of compound of formula 5.
Figure 2:
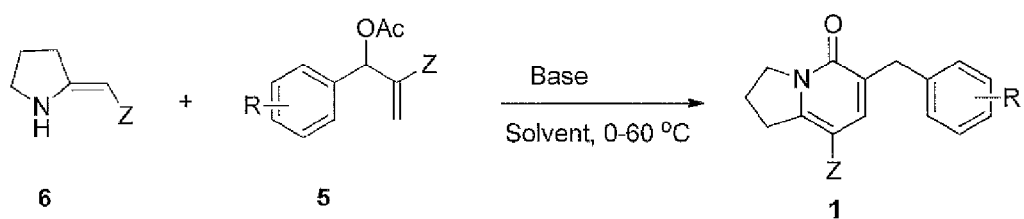
FIG. 2—Scheme 2 illustrates the process for preparation of compound of formula 1.

The precursor substituted aromatic aldehydes 2, activated olefins 3 and 1,4-diazabicyclo[2.2.2]octane (DABCO) are commercially available and indolizinones 1 of formula have been prepared as illustrated in the Schemes (1-2).

i. The substituted aromatic aldehydes 2 reacted with the activated olefins 3 using DABCO at room temperature (25-35° C.) for 10-12 h to obtain desired Baylis-Hillman adducts 4.

ii. To a solution of Baylis-Hillman adducts 4 in dichloromethane at 0° C., under argon atmosphere pyridine was added after 10 min acetyl chloride was added and allow it to stir at room temperature (25-35° C.) for 2 h to obtain desired acetylated Baylis-Hillman adducts 5.

All the indolizinone based derivatives have been synthesized and were purified by column chromatography using solvents like ethyl acetate, hexane, chloroform and methanol.

Procedure of Indolizinone formation: To a solution of NaH (60% in paraffin oil) and dry THF (Z)-ethyl 2-(pyrrolidin-2-ylidene)acetate 6 was added at 0° C. under argon atmosphere and stirred for 15 min. Then acetylated Baylis-Hillman adducts 5 in dry THF was added slowly and allowed to stir at ambient temperature for 3 h. After completion of the reaction solvent was removed under reduced pressure and the residue was diluted with ice cold water and extracted with EtOAc. The combined organic layers were washed with brine, dried over Na₂SO₄, solvent evaporated under reduced pressure and purified by column chromatography by using silica gel with ethylacetate/hexane as eluent.

These new analogues of indolizinone based derivatives were screened for their phosphodiesterase3 (PDE3) inhibition activity and found as potential phosphodiesterase3 inhibitors. The synthesized molecules presented here are of immense biological significance.

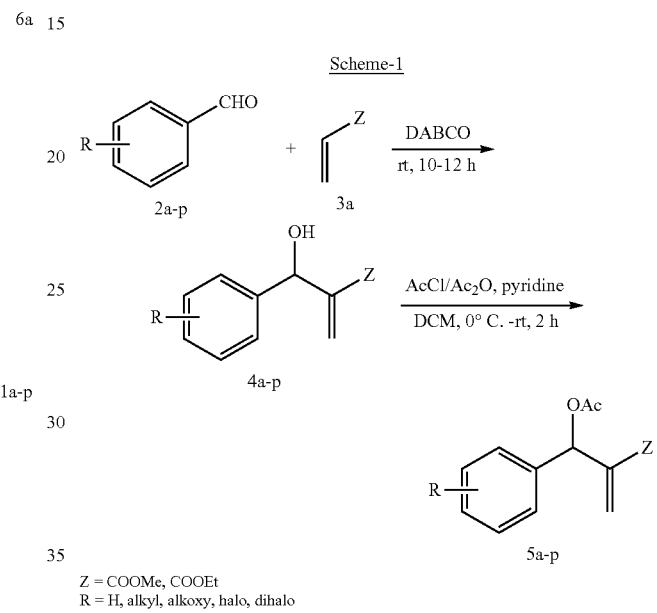

Z = COOMe, COOEt
R = H, alkyl, alkoxy, halo, dihalo

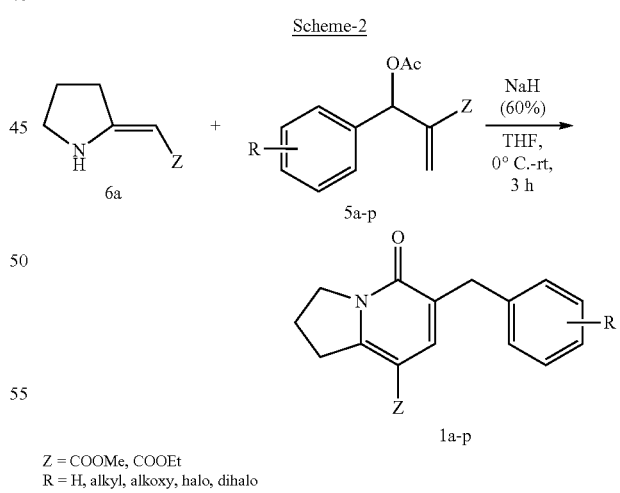

Z = COOMe, COOEt
R = H, alkyl, alkoxy, halo, dihalo

General Procedure for the Preparation Baylis-Hillman Adducts (4a-p)

Substituted aromatic aldehydes (2a-p) (10 mmol), activated olefin (3a-p) (20 mmol) and DABCO (30 mol % with respect to aldehyde) were mixed and allowed to stir at room temperature until completion of the reaction thin layer chromatography (10-12 h). After completion, the reaction mixture was diluted with water (15 mL) and extracted with ether (3×25 mL). The combined organic layers were dried over Na$_2$SO$_4$, solvent was removed under reduced pressure and purified by column chromatography using 10% EtOAc in hexane as eluent to afford pure Baylis-Hillman adducts (4a-p) in 80-90% yield.

IUPAC Names of the Baylis-Hillman Adducts (4a-p)
ethyl 2-(hydroxy(phenyl)methyl)acrylate (4a)
ethyl 2-((2-fluorophenyl)(hydroxy)methyl)acrylate (4b)
ethyl 2-((3-fluorophenyl)(hydroxy)methyl)acrylate (4c)
ethyl 2-((4-fluorophenyl)(hydroxy)methyl)acrylate (4d)
ethyl 2-((2-chlorophenyl)(hydroxy)methyl)acrylate (4e)
ethyl 2-((3-chlorophenyl)(hydroxy)methyl)acrylate (4f)
ethyl 2-((4-chlorophenyl)(hydroxy)methyl)acrylate (4g)
ethyl 2-((2,4-dichlorophenyl)(hydroxy)methyl)acrylate (4h)
ethyl 2-((2-bromophenyl)(hydroxy)methyl)acrylate (4i)
ethyl 2-((3-bromophenyl)(hydroxy)methyl)acrylate (4j)
ethyl 2-((4-bromophenyl)(hydroxy)methyl)acrylate (4k)
ethyl 2-(hydroxy(2-(trifluoromethyl)phenyl)methyl)acrylate (4l)
ethyl 2-(hydroxy(4-(trifluoromethyl)phenyl)methyl)acrylate (4m)
ethyl 2-(hydroxy(p-tolyl)methyl)acrylate (4n)
ethyl 2-((4-ethylphenyl)(hydroxy)methyl)acrylate (4o)
ethyl 2-(hydroxy(4-isopropylphenyl)methyl)acrylate (4p)

General Procedure for the Preparation of Acetylated Baylis-Hillman Adducts (5a-p)

To a well stirred solution of Baylis-Hillman adduct (4a-p) (10 mmol) in dichloromethane (30 mL) at 0° C. under argon atmosphere pyridine (11 mmol) was added slowly and stirred for 10 min. Then acetyl chloride (11 mmol) was added and allowed to stir at room temperature until the reaction completed, thin layer chromatography (1-2 h). After completion of the reaction, diluted the reaction with water (15 mL) and extracted with dichloromethane (2×25 mL). The combined organic layers were washed with sat. CuSO$_4$ solution until pyridine removed, then the layers were separated and dried over Na$_2$SO$_4$, solvent was removed under reduced pressure. The resulting residue was subjected to column chromatography using 5% EtOAc in hexane as eluent to afford pure compounds acetylated Baylis-Hillman adducts (5a-p) in 90-95% yield.

IUPAC Names of the Acetylated Baylis-Hillman Adducts (5a-p)
ethyl 2-(acetoxy(phenyl)methyl)acrylate (5a)
ethyl 2-(acetoxy(2-fluorophenyl)methyl)acrylate (5b)
ethyl 2-(acetoxy(3-fluorophenyl)methyl)acrylate (5c)
ethyl 2-(acetoxy(4-fluorophenyl)methyl)acrylate (5d)
ethyl 2-(acetoxy(2-chlorophenyl)methyl)acrylate (5e)
ethyl 2-(acetoxy(3-chlorophenyl)methyl)acrylate (5f)
ethyl 2-(acetoxy(4-chlorophenyl)methyl)acrylate (5g)
ethyl 2-(acetoxy(2,4-dichlorophenyl)methyl)acrylate (5h)
ethyl 2-(acetoxy(2-bromophenyl)methyl)acrylate (5i)
ethyl 2-(acetoxy(3-bromophenyl)methyl)acrylate (5j)
ethyl 2-(acetoxy(4-bromophenyl)methyl)acrylate (5k)
ethyl 2-(acetoxy(2-(trifluoromethyl)phenyl)methyl)acrylate (5l)
ethyl 2-(acetoxy(4-(trifluoromethyl)phenyl)methyl)acrylate (5m)
ethyl 2-(acetoxy(p-tolyl)methyl)acrylate (5n)
ethyl 2-(acetoxy(4-ethylphenyl)methyl)acrylate (5o)
ethyl 2-(acetoxy(4-isopropylphenyl)methyl)acrylate (5p)

General Procedure for the Preparation of Indolizinone Derivatives (1)

To a well stirred solution of base (3 mmol) and dry solvent (5 mL) (Z)-ethyl 2-(pyrrolidin-2-ylidene)acetate (6) (1 mmol) was added slowly at 0° C. under inert atmosphere and stirred for 15 min. Then acetylated Baylis-Hillman addu (5) (1 mmol) was added slowly and allowed to stir at ambient temperature for 3 h and the reaction was monitored by TLC. After completion, solvent was removed under reduced pressure and the residue was diluted with ice cold water (5 mL) and extracted with EtOAc (3×10 mL). The combined organic layers were washed with brine, dried over Na$_2$SO$_4$, evaporated in vacuo and purified by column chromatography using silica gel with 30% EtOAc in hexane as eluent to obtained 1.

The following examples are given by way of illustration

Example 1

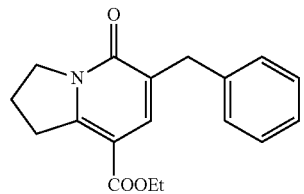

Ethyl 6-benzyl-5-oxo-1,2,3,5-tetrahydro-8-indolizinonecarboxylate (1a)

To a well stirred solution of NaH (60% in paraffin oil, 115 mg, 3 mmol) and dry THF (5 mL) (Z)-ethyl 2-(pyrrolidin-2-ylidene)acetate (6a) (155 mg, 1 mmol) was added slowly at 0° C. under argon atmosphere and stirred for 15 min. Then ethyl 2-(acetoxy(phenyl)methyl)acrylate (5a) (246 mg, 1 mmol) was added slowly and allowed to stir at ambient temperature for 3 h and the reaction was monitored by TLC. After completion, solvent was removed under reduced pressure and the residue was diluted with ice cold water (5 mL) and extracted with EtOAc (3×10 mL). The combined organic layers were washed with brine, dried over Na$_2$SO$_4$, evaporated in vacuo and purified by column chromatography using silica gel with 30% EtOAc in hexane as eluent to obtained 1a as white solid (212 mg, 72% yield).

$^1$H NMR (300 MHz, CDCl$_3$): δ 7.62 (s, 1H), 7.25-7.14 (m, 4H), 4.25 (q, J=7.0 Hz, 2H), 4.14 (t, J=7.5 Hz, 2H), 3.80 (s, 2H), 3.49 (t, J=7.9 Hz, 2H), 2.26-2.16 (m, 2H), 1.33 (t, J=Hz, J=7.0 Hz, 3H); $^{13}$C NMR (75 MHz, CDCl$_3$): δ 165.0, 161.9, 155.0, 139.5, 137.4, 129.1, 129.0, 128.4, 126.2, 105.4, 60.6, 49.2, 36.0, 33.6, 20.8, 14.3; MS (ESI): m/z 298 [M+H]$^+$; HRMS (ESI): m/z [M+H]$^+$ calculated for C$_{18}$H$_{20}$NO$_3$: 298.1443; found: 298.1456.

Example 2

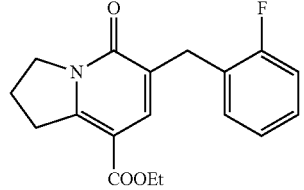

Ethyl 6-(2-fluorobenzyl)-5-oxo-1,2,3,5-tetrahydro-8-indolizinonecarboxylate (1b)

To a well stirred solution of NaH (60% in paraffin oil, 115 mg, 3 mmol) and dry THF (5 mL) (Z)-ethyl 2-(pyrrolidin-2-ylidene)acetate (6a) (155 mg, 1 mmol) was added slowly at 0° C. under argon atmosphere and stirred for 15 min. Then ethyl 2-(acetoxy(2-fluorophenyl)methyl)acrylate (5b) (264 mg, 1 mmol) (5 mL) was added slowly and allowed to stir at ambient temperature for 3 h and the reaction was monitored by TLC. After completion, solvent was removed under reduced pressure and the residue was diluted with ice cold water (5 mL) and extracted with EtOAc (3×10 mL). The combined organic layers were washed with brine, dried over $Na_2SO_4$, evaporated in vacuo and purified by column chromatography using silica gel with 30% EtOAc in hexane as eluent to obtained 1b as pale yellow solid (234 mg, 75% yield).

$^1$H NMR (75 MHz, $CDCl_3$): δ 7.66 (s, 1H), 7.36-6.96 (m, 4H), 4.25 (q, J=7.0 Hz, 3H), 4.14 (t, J=7.5 Hz, 2H), 3.84 (s, 2H), 3.49 (t, J=7.9 Hz, 2H), 2.26-2.19 (m, 3H), 1.33 (t, J=7.0 Hz, 3H); $^{13}$C NMR (75 MHz, $CDCl_3$): δ 161.8, 155.3, 137.7, 129.6, 128.2, 124.6, 124.6, 115.8, 115.5, 113.2, 112.9, 105.4, 60.6, 49.2, 35.7, 33.6, 20.7, 14.3; MS (ESI): m/z 316 [M+H]$^+$; HRMS (ESI): m/z [M+H]$^+$ calculated for $C_{18}H_{19}NO_3F$: 316.1348; found: 316.1353.

Example 3

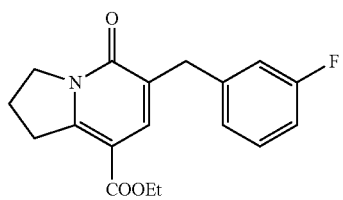

1c

Ethyl 6-(3-fluorobenzyl)-5-oxo-1,2,3,5-tetrahydro-8-indolizinonecarboxylate (1c)

To a well stirred solution of NaH (60% in paraffin oil, 115×mg, 3 mmol) and dry THF (5 mL) (Z)-ethyl 2-(pyrrolidin-2-ylidene)acetate (6a) (155 mg, 1 mmol) was added slowly at 0° C. under argon atmosphere and stirred for 15 min. Then ethyl 2-(acetoxy(3-fluorophenyl)methyl)acrylate (5c) (264 mg, 1 mmol) was added slowly and allowed to stir at ambient temperature for 3 h and the reaction was monitored by TLC. After completion, solvent was removed under reduced pressure and the residue was diluted with ice cold water (5 mL) and extracted with EtOAc (3×10 mL). The combined organic layers were washed with brine, dried over $Na_2SO_4$, evaporated in vacuo and purified by column chromatography using silica gel with 30% EtOAc in hexane as eluent to obtained 3c as pale yellow solid (229 mg, 73% yield).

$^1$H NMR (300 MHz, $CDCl_3$): δ 7.73 (s, 1H), 7.27-6.85 (m, 4H), 4.29 (q, J 7.1 Hz, 2H), 4.16 (t, J=7.1 Hz, 2H), 3.84 (s, 2H), 3.51 (t, J=7.7 Hz, 2H), 2.26-2.16 (m, 2H), 1.34 (t, J=7.1 Hz, 3H); $^{13}$C NMR (75 MHz, $CDCl_3$): δ 164.9, 161.8, 155.4, 137.7, 129.8, 129.7, 128.2, 124.6, 115.6, 113.3, 113.0, 60.7, 49.3, 35.8, 33.7, 20.8, 14.4; MS (ESI): m/z 316 [M+H]$^+$; HRMS (ESI): m/z [M+H]$^+$ calculated for $C_{18}H_{19}NO_3F$: 316.1348; found: 316.1336.

Example 4

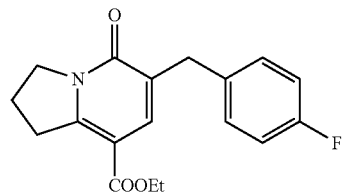

1d

Ethyl 6-(4-fluorobenzyl)-5-oxo-1,2,3,5-tetrahydro-8-indolizinonecarboxylate (1d)

To a well stirred solution of NaH (60% in paraffin oil, 115 mg, 3 mmol) and dry THF (5 mL) (Z)-ethyl 2-(pyrrolidin-2-ylidene)acetate (6a) (155 mg, 1 mmol) was added slowly at 0° C. under argon atmosphere and stirred for 15 min. Then ethyl 2-(acetoxy(4-fluorophenyl)methyl)acrylate (5d) (264 mg, 1 mmol) was added slowly and allowed to stir at ambient temperature for 3 h and the reaction was monitored by TLC. After completion, solvent was removed under reduced pressure and the residue was diluted with ice cold water (5 mL) and extracted with EtOAc (3×10 mL). The combined organic layers were washed with brine, dried over $Na_2SO_4$, evaporated in vacuo and purified by column chromatography using silica gel with 30% EtOAc in hexane as eluent to obtained 1d as ash colour solid (238 mg, 76% yield).

$^1$H NMR (300 MHz, $CDCl_3$): δ 7.69 (s, 1H), 7.27-6.91 (m, 4H), 4.28 (q, J 7.1 Hz, 2H), 4.15 (t, J=7.3 Hz, 2H), 3.80 (s, 2H), 3.50 (t, J=7.9 Hz, 2H), 2.26-2.15 (m, 2H), 1.34 (t, J=7.1 Hz, 3H). $^{13}$C NMR (75 MHz, $CDCl_3$): δ 164.9, 161.8, 155.1, 137.3, 130.4, 130.3, 128.8, 115.2, 114.9, 105.4, 60.6, 49.2, 35.3, 33.6, 20.7, 14.3; MS (EST): m/z 316 [M+H]$^+$; HRMS (ESI): m/z [M+H]$^+$ calculated for $C_{18}H_{19}NO_3F$: 316.1348; found: 316.1335.

Example 5

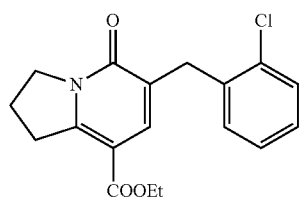

1e

Ethyl 6-(2-chlorobenzyl)-5-oxo-1,2,3,5-tetrahydro-8-indolizinonecarboxylate (1e)

To a well stirred solution of NaH (60% in paraffin oil, 115 mg, 3 mmol) and dry THF (5 mL) (Z)-ethyl 2-(pyrrolidin-2-ylidene)acetate (6a) (155 mg, 1 mmol) was added slowly at 0° C. under argon atmosphere and stirred for 15 min. Then ethyl 2-(acetoxy(2-chlorophenyl)methyl)acrylate (5e) (280 mg, 1 mmol) was added slowly and allowed to stir at ambient temperature for 3 h and the reaction was monitored by TLC. After completion, solvent was removed under reduced pressure and the residue was diluted with ice cold water (5 mL) and extracted with EtOAc (3×10 mL). The combined organic layers were washed with brine, dried over Na$_2$SO$_4$, evaporated in vacuo and purified by column chromatography using silica gel with 30% EtOAc in hexane as eluent to obtained 1e as ash colour solid (240 mg, 73% yield).

$^1$H NMR (300 MHz, CDCl$_3$): δ 7.61 (s, 1H), 7.36-7.10 (m, 4H), 4.24 (q, J 6.7 Hz, 2H), 4.15 (t, J=7.5 Hz, 2H), 3.93 (s, 2H), 3.49 (t, J=8.3 Hz, 2H), 2.27-2.16 (m, 2H), 1.31 (t, J=6.7 Hz, 3H); $^{13}$C NMR (75 MHz, CDCl$_3$): δ 164.9, 161.8, 155.0, 137.7, 136.7, 134.3, 131.4, 129.4, 127.8, 127.0, 126.7, 105.4, 60.6, 49.2, 33.6, 33.5, 20.7, 14.3; MS (ESI): m/z 332 [M+H]$^+$; HRMS (ESI): m/z [M+H]$^+$ calculated for C$_{18}$H$_{19}$NO$_3$Cl: 332.1053; found: 332.1038.

Example 6

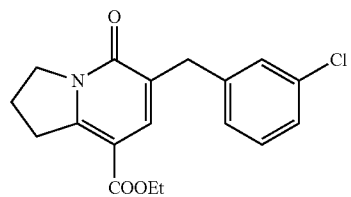

Ethyl 6-(3-chlorobenzyl)-5-oxo-1,2,3,5-tetrahydro-8-indolizinonecarboxylate (1f)

To a well stirred solution of NaH (60% in paraffin oil, 115 mg, 3 mmol) and dry THF (5 mL) (Z)-ethyl 2-(pyrrolidin-2-ylidene)acetate (6a) (155 mg, 1 mmol) was added slowly at 0° C. under argon atmosphere and stirred for 15 min. Then ethyl 2-(acetoxy(3-chlorophenyl)methyl)acrylate (5f) (280 mg, 1 mmol) was added slowly and allowed to stir at ambient temperature for 3 h and the reaction was monitored by TLC. After completion, solvent was removed under reduced pressure and the residue was diluted with ice cold water (5 mL) and extracted with EtOAc (3×10 mL) The combined organic layers were washed with brine, dried over Na$_2$SO$_4$, evaporated in vacuo and purified by column chromatography using silica gel with 30% EtOAc in hexane as eluent to obtained 1f as ash colour solid (230 mg, 70% yield).

$^1$H NMR (300 MHz, CDCl$_3$): δ 7.71 (s, 1H), 7.26-7.15 (m, 41-1), 4.29 (q, J=7.0 Hz, 2H), 4.15 (t, J=7.3 Hz, 2H), 3.81 (s, 2H), 3.51 (t, J=7.9 Hz, 2H), 2.26-2.16 (m, 2H), 1.35 (t, J=7.0 Hz, 3H); $^{13}$C NMR (75 MHz, CDCl$_3$): δ 164.9, 161.7, 155.4, 141.5, 137.7, 134.0, 129.6, 128.8, 128.0, 127.2, 126.4, 105.4, 60.7, 49.5, 35.7, 33.7, 20.7, 14.3; MS (ESI): m/z 332 [M+H]$^+$; HRMS (ESI): m/z [M+H]$^+$ calculated for C$_{18}$H$_{19}$NO$_3$Cl: 332.1053; found: 332.1045.

Example 7

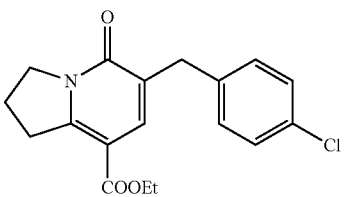

Ethyl 6-(4-chlorobenzyl)-5-oxo-1,2,3,5-tetrahydro-8-indolizinonecarboxylate (1g)

To a well stirred solution of NaH (60% in paraffin oil, 115 mg, 3 mmol) and dry THF (5 mL) (Z)-ethyl 2-(pyrrolidin-2-ylidene)acetate (6a) (155 mg, 1 mmol) was added slowly at 0° C. under argon atmosphere and stirred for 15 min. Then ethyl 2-(acetoxy(4-chlorophenyl)methyl)acrylate (5g) (280 mg, 1 mmol) was added slowly and allowed to stir at ambient temperature for 3 h and the reaction was monitored by TLC. After completion, solvent was removed under reduced pressure and the residue was diluted with ice cold water (5 mL) and extracted with EtOAc (3×10 mL). The combined organic layers were washed with brine, dried over Na$_2$SO$_4$, evaporated in vacuo and purified by column chromatography by using silica gel with 30% EtOAc in hexane as eluent to obtained 1 g as ash colour solid (267 mg, 81% yield).

$^1$H NMR (300 MHz, CDCl$_3$): δ 7.70 (s, 1H), 7.22 (s, 4H), 4.28 (q, J=6.9 Hz, 2H), 4.14 (t, J=7.3 Hz, 2H), 3.79 (s, 2H), 3.50 (t, J=7.9 Hz, 2H), 2.26-2.15 (m, 2H), 1.34 (t, J=7.1 Hz, 3H); $^{13}$C NMR (75 MHz, CDCl$_3$): δ 164.9, 161.8, 155.3, 138.0, 137.5, 137.3, 132.0, 130.3, 128.4, 105.4, 60.67, 49.3, 35.5, 33.7, 20.8, 14.3; MS (ESI): 332 [M+H]$^+$; HRMS (ESI): m/z [M+H]$^+$ calculated for C$_{18}$H$_{20}$NO$_3$Cl: 332.1053; found: 332.1051.

Example 8

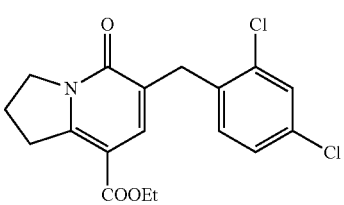

Ethyl 6-(2,4-dichlorobenzyl)-5-oxo-1,2,3,5-tetrahydro-8-indolizinonecarboxylate (1h)

To a well stirred solution of NaH (60% in paraffin oil, 115 mg, 3 mmol) and THF (5 mL) (Z)-ethyl 2-(pyrrolidin-2-ylidene)acetate (6a) (155 mg, 1 mmol) was added slowly at 0° C. under argon atmosphere and stirred for 15 min. Then ethyl 2-(acetoxy(2,4-dichlorophenyl)methyl)acrylate (5h) (315 mg, 1 mmol) was added slowly and allowed to stir at ambient temperature for 3 h and the reaction was monitored by TLC. After completion, solvent was removed under reduced pressure and the residue was diluted with ice cold water (5 mL) and extracted with EtOAc (3×10 mL). The combined organic layers were washed with brine, dried over Na$_2$SO$_4$, evaporated in vacuo and purified by column chromatography using silica gel with 30% EtOAc in hexane as eluent to obtained 1h as ash colour solid (280 mg, 77% yield).

$^1$H NMR (500 MHz, CDCl$_3$): δ 7.69 (s, 1H), 7.37-7.15 (m, 3H), 4.28 (q, J=7.5 Hz, 2H), 4.16 (t, J=7.5 Hz, 2H), 3.92 (s, 2H), 3.51 (t, J 8.3 Hz, 2H), 2.26-2.16 (m, 2H), 1.33 (t, J=7.5 Hz, 3H); $^{13}$C NMR (50 MHz, CDCl$_3$): δ 164.5, 161.4, 155.0, 137.7, 135.1, 134.6, 132.4, 131.9, 128.9, 126.7, 126.1, 105.2, 60.4, 49.0, 33.4, 32.9, 20.5, 14.1; MS (ESI): m/z 366 [M+H]$^+$; HRMS (ESI): m/z [M+H]$^+$ calculated for C$_{18}$H$_{18}$NO$_3$Cl$_2$: 366.0663; found: 316.0654.

Example 9

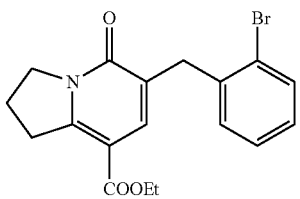

1i

Ethyl 6-(2-bromobenzyl)-5-oxo-1,2,3,5-tetrahydro-8-indolizinonecarboxylate (1i)

To a well stirred solution of NaH (60% in paraffin oil, 115 mg, 3 mmol) and THF (5 mL) (Z)-ethyl 2-(pyrrolidin-2-ylidene)acetate (6a) (155 mg, 1 mmol) was added slowly at 0° C. under argon atmosphere and stirred for 15 min. Then ethyl 2-(acetoxy(2-bromophenyl)methyl)acrylate (5i) (324 mg, 1 mmol) was added slowly and allowed to stir at ambient temperature for 3 h and the reaction was monitored by TLC. After completion, solvent was removed under reduced pressure and the residue was diluted with ice cold water (5 mL) and extracted with EtOAc (3×10 mL). The combined organic layers were washed with brine, dried over Na$_2$SO$_4$, evaporated in vacuo and purified by column chromatography using silica gel with 30% EtOAc in hexane as eluent to obtained 1i as ash colour solid (291 mg, 78% yield).

$^1$H NMR (300 MHz, CDCl$_3$): δ 7.64 (s, 1H), 7.56-7.05 (m, 4H), 4.25 (q, J=7.1 Hz, 2H), 4.18 (t, J=7.5 Hz, 2H), 3.97 (s, 2H), 3.50 (t, J=8.3 Hz, 2H), 2.27-2.16 (m, 2H), 1.31 (t, J=7.1 Hz, 3H); $^{13}$C NMR (75 MHz, CDCl$_3$): δ 164.9, 161.8, 155.7, 138.4, 137.8, 132.8, 131.4, 128.0, 127.4, 127.0, 124.9, 105.4, 60.6, 49.3, 35.9, 33.6, 20.8, 14.3; MS (EST): m/z 376 [M+H]$^+$; HRMS (ESI): m/z [M+H]$^+$ calculated for C$_{18}$H$_{19}$NO$_3$Br: 376.0548; found: 376.0537.

Example 10

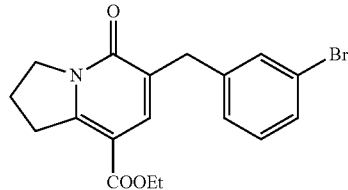

1j

Ethyl 6-(3-bromobenzyl)-5-oxo-1,2,3,5-tetrahydro-8-indolizinonecarboxylate (1j)

To a well stirred solution of NaH (60% in paraffin oil, 115 mg, 3 mmol) and THF (5 mL) (Z)-ethyl 2-(pyrrolidin-2-ylidene)acetate (6a) (155 mg, 1 mmol) was added slowly at 0° C. under argon atmosphere and stirred for 15 min. Then ethyl 2-(acetoxy(3-bromophenyl)methyl)acrylate (5j) (324 mg, 1 mmol) was added slowly and allowed to stir at ambient temperature for 3 h and the reaction was monitored by TLC. After completion, solvent was removed under reduced pressure and the residue was diluted with ice cold water (5 mL) and extracted with EtOAc (3×10 mL). The combined organic layers were washed with brine, dried over Na$_2$SO$_4$, evaporated in vacuo and purified by column chromatography using silica gel with 30% EtOAc in hexane as eluent to obtained 1j as white solid (280 mg, 75% yield).

$^1$H NMR (300 MHz, CDCl$_3$+DMSO-d$_6$): δ 7.72 (s, 1H), 7.41-7.11 (m, 4H), 4.29 (q, J=7.1 Hz, 2H), 4.15 (t, J=7.5 Hz, 2H), 3.80 (s, J=7.5 Hz, 2H), 3.51 (t, J=7.5 Hz, 2H), 2.26-2.16 (m, 2H), 1.35 (t, J 7.1 Hz, 3H); $^{13}$C NMR (75 MHz, CDCl$_3$): δ 164.9, 161.8, 155.5, 141.9, 137.8, 131.8, 129.9, 129.4, 128.1, 127.8, 122.4, 105.4, 60.7, 49.3, 35.8, 33.7, 20.8, 14.4; MS (ESI): m/z 376 [M+H]$^+$; HRMS (ESI): m/z [M+H]$^+$ calculated for C$_{18}$H$_{19}$NO$_3$Br: 376.0548; found: 376.0533.

Example 11

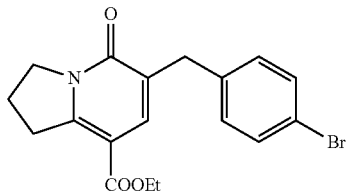

1k

Ethyl 6-(4-bromobenzyl)-5-oxo-1,2,3,5-tetrahydro-8-indolizinonecarboxylate (1k)

To a well stirred solution of NaH (60% in paraffin oil, 115 mg, 3 mmol) and THF (5 mL) (Z)-ethyl 2-(pyrrolidin-2-ylidene)acetate (6a) (155 mg, 1 mmol) was added slowly at 0° C. under argon atmosphere and stirred for 15 min. Then ethyl 2-(acetoxy(4-bromophenyl)methyl)acrylate (5k) (324 mg, 1 mmol) was added slowly and allowed to stir at ambient temperature for 3 h and the reaction was monitored by TLC. After completion, solvent was removed under reduced pressure and the residue was diluted with ice cold water (5 mL) and extracted with EtOAc (3×10 mL). The combined organic layers were washed with brine, dried over Na$_2$SO$_4$, evaporated in vacuo and purified by column chromatography using silica gel with 30% EtOAc in hexane as eluent to obtained 1k as white solid (295 mg, 79% yield).

$^1$H NMR (300 MHz, CDCl$_3$): δ 7.70 (s, 1H), 7.39-7.15 (m, 4H), 4.29 (q, J=7.5 Hz, 2H), 4.14 (t, J=6.9 Hz, 2H), 3.78 (s, 2H), 3.50 (t, J=8.3 Hz, 2H), 2.25-2.15 (m, 2H), 1.34 (t, J=7.5 Hz, 3H); $^{13}$C NMR (75 MHz, CDCl$_3$): δ 164.9, 161.7, 155.3, 138.5, 137.5, 131.4, 130.7, 128.3, 120.0, 105.4, 60.6, 49.2, 35.6, 33.6, 20.7, 14.3; MS (EST): 376 [M+H]$^+$; HRMS (ESI): m/z [M+H]$^+$ calculated for C$_{18}$H$_{19}$NO$_3$Br: 376.0548; found: 376.0533.

Example 12

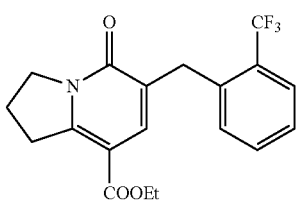

Ethyl 5-oxo-6-[2-(trifluoromethyl)benzyl]-1,2,3,5-tetrahydro-8-indolizinonecarboxylate (1l)

To a well stirred solution of NaH (60% in paraffin oil, 115 mg, 3 mmol) and THF (5 mL) (Z)-ethyl 2-(pyrrolidin-2-ylidene)acetate (6a) (155 mg, 1 mmol) was added slowly at 0° C. under argon atmosphere and stirred for 15 min. Then ethyl 2-(acetoxy(2-(trifluoromethyl)phenyl)methyl)acrylate (5l) (314 mg, 1 mmol) was added slowly and allowed to stir at ambient temperature for 3 h and the reaction was monitored by TLC. After completion, solvent was removed under reduced pressure and the residue was diluted with ice cold water (5 mL) and extracted with EtOAc (3×10 mL). The combined organic layers were washed with brine, dried over Na$_2$SO$_4$, evaporated in vacuo and purified by column chromatography using silica gel with 30% EtOAc in hexane as eluent to obtained 1l as ash colour solid (258 mg, 71% yield).

$^1$H NMR (500 MHz, CDCl$_3$): δ 7.66-7.25 (m, 5H), 4.24-4.16 (m, 4H), 4.03 (s, 2H), 3.51 (t, J=7.8 Hz, 2H), 2.26-2.20 (m, 2H), 1.29 (t, J=7.8 Hz, 3H); $^{13}$C NMR (75 MHz, CDCl$_3$): δ 164.8, 161.8, 155.1, 137.9, 137.8, 131.8, 131.5, 127.9, 126.4, 126.0, 125.9, 105.4, 60.5, 49.3, 33.6, 32.0, 20.7, 14.2; MS (ESI): m/z 366 [M+H]$^+$; HRMS (ESI): m/z [M+H]$^+$ calculated for C$_{19}$H$_{19}$NO$_3$F$_3$: 366.1317; found: 366.1308.

Example 13

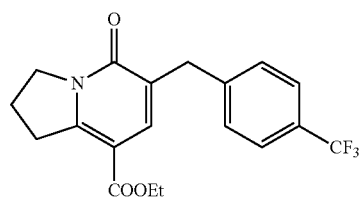

Ethyl 5-oxo-6-[4-(trifluoromethyl)benzyl]-1,2,3,5-tetrahydro-8-indolizinonecarboxylate (1m)

To a well stirred solution of NaH (60% in paraffin oil, 115 mg, 3 mmol) and THF (5 mL) (Z)-ethyl 2-(pyrrolidin-2-ylidene)acetate (6a) (155 mg, 1 mmol) was added slowly at 0° C. under argon atmosphere and stirred for 15 min. Then ethyl 2-(acetoxy(4-(trifluoromethyl)phenyl)methyl)acrylate (5m) (314 mg, 1 mmol) was added slowly and allowed to stir at ambient temperature for 3 h and the reaction was monitored by TLC. After completion, solvent was removed under reduced pressure and the residue was diluted with ice cold water (5 mL) and extracted with EtOAc (3×10 mL). The combined organic layers were washed with brine, dried over Na$_2$SO$_4$, evaporated in vacuo and purified by column chromatography using silica gel with 30% EtOAc in hexane as eluent to obtained 1 m as ash colour solid (269 mg, 74% yield).

$^1$H NMR (300 MHz, CDCl$_3$): δ 7.74-7.26 (m, 5H), 4.29 (q, J=7.1 Hz, 2H), 4.15 (t, J=7.5 Hz, 2H), 3.88 (s, 2H), 3.51 (t, J=7.9 Hz, 2H), 2.26-2.16 (m, 2H), 1.35 (t, J=7.1 Hz, 3H); $^{13}$C NMR (75 MHz, CDCl$_3$): δ 164.8, 161.7, 155.5, 143.6, 137.8, 129.1, 128.7, 127.9, 125.3, 125.2, 105.4, 60.7, 49.2, 36.0, 33.7, 20.7, 14.3; MS (ESI): m/z 366 [M+H]$^+$; HRMS (ESI): m/z [M+H]$^+$ calculated for C$_{19}$H$_{19}$NO$_3$F$_3$: 366.1317; found: 366.1311.

Example 14

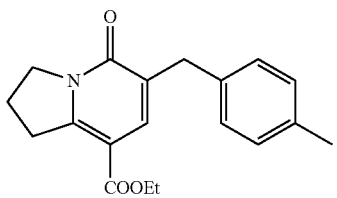

Ethyl 6-(4-methylbenzyl)-5-oxo-1,2,3,5-tetrahydro-8-indolizinonecarboxylate (1n)

To a well stirred solution of NaH (60% in paraffin oil, 115 mg, 3 mmol) and THF (5 mL) (Z)-ethyl 2-(pyrrolidin-2-ylidene)acetate (6a) (155 mg, 1 mmol) was added slowly at 0° C. under argon atmosphere and stirred for 15 min. Then ethyl 2-(acetoxy(p-olyl)methyl)acrylate (5n) (260 mg, 1 mmol)

was added slowly and allowed to stir at ambient temperature for 3 h and the reaction was monitored by TLC. After completion, solvent was removed under reduced pressure and the residue was diluted with ice cold water (5 mL) and extracted with EtOAc (3×10 mL) The combined organic layers were washed with brine, dried over Na$_2$SO$_4$, evaporated in vacuo and purified by column chromatography using silica gel with 30% EtOAc in hexane as eluent to obtained 1 n as pale yellow solid (241 mg, 78% yield).

$^1$H NMR (300 MHz, CDCl$_3$): δ 7.68 (s, 1H), 7.19-7.06 (m, 4H), 4.27 (q, J=7.1 Hz, 2H), 4.14 (t, J=7.5 Hz, 2H), 3.80 (s, 2H), 3.48 (t, J=8.3 Hz, 2H), 2.30 (s, 3H), 2.24 (m, 2H), 1.33 (t, J=7.1 Hz, 3H); $^{13}$C NMR (75 MHz, CDCl$_3$): δ 165.0, 161.9, 154.9, 137.3, 137.1, 136.4, 135.6, 129.1, 128.8, 105.4, 60.6, 49.2, 35.6, 33.6, 21.0, 20.8, 14.3; MS (ESI): m/z 312 [M+H]$^+$; HRMS (EST): m/z [M+H]$^+$ calculated for C$_{19}$H$_{22}$NO$_3$: 312.1599; found: 312.1614.

Example 15

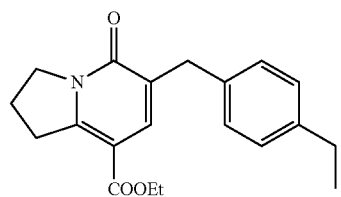

Ethyl 6-(4-ethylbenzyl)-5-oxo-1,2,3,5-tetrahydro-8-indolizinonecarboxylate (1o)

To a well stirred solution of NaH (60% in paraffin oil, 115×mg, 3 mmol) and THF (5 mL) (Z)-ethyl 2-(pyrrolidin-2-ylidene)acetate (6a) (155 mg, 1 mmol) was added slowly at 0° C. under argon atmosphere and stirred for 15 min. Then ethyl 2-(acetoxy(4-ethylphenyl)methyl)acrylate (5o) (274 mg, 1 mmol) was added slowly and allowed to stir at ambient temperature for 3 h and the reaction was monitored by TLC. After completion, solvent was removed under reduced pressure and the residue was diluted with ice cold water (5 mL) and extracted with EtOAc (3×10 mL). The combined organic layers were washed with brine, dried over Na$_2$SO$_4$, evaporated in vacuo and purified by column chromatography using silica gel with 30% EtOAc in hexane as eluent to obtained 1o as ash colour (242 mg, 75% yield).

$^1$H NMR (500 MHz, CDCl$_3$): δ 7.68 (s, 1H), 7.20-7.09 (m, 4H), 4.27 (q, J=7.2 Hz, 2H), 4.14 (t, J=7.2 Hz, 2H), 3.80 (s, 2H), 3.48 (t, J=8.2 Hz, 2H), 2.60 (q, J=7.2 Hz, 2H), 2.22-2.16 (m, 2H), 1.32 (t, J=7.2 Hz, 3H), 1.20 (t, J=8.2 Hz, 3H); $^{13}$C NMR (75 MHz, CDCl$_3$): δ 165.0, 161.9, 154.9, 142.0, 137.3, 136.6, 129.3, 128.9, 127.9, 105.4, 60.6, 49.2, 35.6, 33.6, 28.4, 20.8, 15.6, 14.3; MS (ESI): m/z 326[M+H]$^+$; HRMS (ESI): m/z [M+H]$^+$ calculated for C$_{20}$H$_{24}$NO$_3$: 326.1756; found: 326.1769.

Example 16

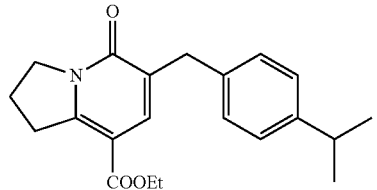

Ethyl 6-(4-isopropylbenzyl)-5-oxo-1,2,3,5-tetrahydro-8-indolizinonecarboxylate (1p)

To a well stirred solution of NaH (60% in paraffin oil, 115 mg, 3 mmol) and THF (5 mL) (Z)-ethyl 2-(pyrrolidin-2-ylidene)acetate (6a) (155 mg, 1 mmol) was added slowly at 0° C. under argon atmosphere and stirred for 15 min. Then ethyl 2-(acetoxy(4-isopropylphenyl)methyl)acrylate (5p) (288 mg, 1 mmol) was added slowly and allowed to stir at ambient temperature for 3 h and the reaction was monitored by TLC. After completion, solvent was removed under reduced pressure and the residue was diluted with ice cold water (5 mL) and extracted with EtOAc (3×10 mL). The combined organic layers were washed with brine, dried over Na$_2$SO$_4$, evaporated in vacuo and purified by column chromatography using silica gel with 30% EtOAc in hexane as eluent to obtained 1p as pale yellow solid (239 mg, 71% yield).

$^1$H NMR (500 MHz, CDCl$_3$): δ 7.68 (s, 1H), 7.21-7.12 (m, 4H), 4.26 (q, J=7.2 Hz, 2H), 4.15 (t, J=7.2 Hz, 2H), 3.80 (s, 2H), 3.48 (t, J=8.2 Hz, 2H), 2.88-2.83 (m, J=7.2 Hz, 1H), 2.22-2.16 (m, 2H), 1.32 (t, J=6.3 H$_z$, 3H), 1.22 (d, J=6.3 Hz, 6H); $^{13}$C NMR (75 MHz, CDCl$_3$): δ 165.0, 161.9, 154.9, 146.6, 137.3, 136.7, 129.2, 128.8, 126.4, 105.3, 60.5, 49.2, 35.5, 33.7, 33.6, 23.9, 20.7, 14.2; MS (EST): m/z 340 [M+H]$^+$; HRMS (ESI): m/z [M+H]$^+$ calculated for C$_{21}$H$_{26}$NO$_3$: 340.1912; found: 340.1906.

PHARMACOLOGY

Milrinone, a known PDE3 inhibitor, drug has been used as standard for comparison with the inhibitory activity of synthesized new analogues 1a-p. Milrinone is a nonsympathomimetic and nonglycosidic drug that increases myocardial contraction. It increases myocardial cyclic adenosine monophosphate (c-AMP) concentration by selective inhibition of cardiac phosphodiesterase3 (PDE3) enzymes and increases intracellular calcium level, thereby increasing myocardial contractility (Weishaar R E, Quade M M, Schenden J A, Evans D B. Relationship between inhibition of cardiac muscle phosphodiesterase, changes in cyclic nucleotide levels, and contractile response for C1-914 and other novel cardiotonics. (J Cyclic Nucleotide Protein Phosphor Res 1985; 10:551-64). All PDE3 inhibitors has beneficial effects on the acute treatment of congestive heart failure (Bairn D S, McDowell A V, Chemiles J, et al. Evaluation of a new bipyridine inotropic agent-milrinone-in patients with severe congestive heart failure. N Engl J Med 1983; 309:748-56) and offers an important therapeutic option for left ventricular failure in patients undergoing cardiac surgery because of its unique inodilator effects. PDE3 enzymes are present not only in cardiac muscle but it also present in platelets. In platelets, c-AMP generated from adenosine triphosphate by adenyl cyclase serves as an intracellular second messenger to inhibit the platelet activation at numerous steps (Campbell F W, Addonizo V P Jr. Platelet function alterations during cardiac surgery. In: Ellison N, Jobes D R, ed. Effective hemostasis in cardiac surgery. Philadelphia: WB Saunders, 1988: 93-5). Since abnormal bleeding after cardiopulmonary bypass (CPB) is most often due to an acute acquired defect in platelets (Harker L. Bleeding after cardiopulmonary bypass. N Engl J Med 1986; 314:1446-8), preservation of platelet function is critical to maintaining normal hemostasis in patients undergoing cardiac surgery.

The commercially utility of the compounds according to the invention have valuable pharmacological properties. As selective inhibitors of type 3 of cyclic nucleotide phosphodiesterase3 (PDE3), they are suitable for heart failure therapy as well as anti-thrombotic (platelet aggregation-inhibiting) therapy.

BIOLOGICAL INVESTIGATIONS

PDE3 inhibition assay was performed a BIOMOL GREEN™ Quantizyme Assay System (catalogue No. BML-AK800-0001). The Platelets isolated from human blood were used as a source of PDE3 enzyme. 10 mL blood collected in a vacutainer tube (containing $K_3$ EDTA) and centrifuged at 190×g for 15 min at room temperature. Top layer (platelet rich plasma) collected, centrifuged at 2500g for 5 min at 22° C. (Room temp.) The pellet was washed with 2 ml of 50 mM tris buffer (pH-7.4) containing 1 mM $MgCl_2$ and centrifuged at 2500 g for 5 min. Then 200 µl of assay buffer (from PDE kit, Enzo Life Sciences) was added to the pellet and sonicated at 30 s per ml. Pellet was freeze thawed for three times (−80° C.) in order to rupture the platelet membrane and release the PDE enzyme. Then the cell homogenate was centrifuged at 2500 rpm for 5 min. Supernatant was collected and used as source for PDE3 enzyme. In 96 well plate (Prod. No. BML-KI101), we added supernatant having PDE3 enzyme, PDE3 assay buffer, cAMP substrate, 5'nucleotidase and test or standard compound and incubated for 1 hour at 37° C. The reaction was arrested by the addition 100 µl BIOMOL GREEN reagent incubated in room temp for 20 min. The green color developed was measured at 620 nm

METHODOLOGY

The in vitro Phosphodiestarase (PDE3) inhibitory activity of compounds 1a-p were measured using a BIOMOL GREEN™ Quantizyme Assay System (catalogue No. BML-AK800-0001). The basic principle for this assay is the cleavage of c-AMP or c-GMP into their respective nucleotide by a cyclic nucleotide phosphodiesterase. The nucleotide (AMP or GMP) released is further cleaved into the nucleoside and phosphate by the enzyme 5'-nucleotidase. The extent of phosphate released is directly proportional to the PDE activity. In this screening method, the released phosphate by the enzymatic cleavage is quantified using BIOMOL GREEN reagent in a modified malachite green assay. The resulting green colour with λmax at 620 nm is directly proportional to the released phosphate and then PDE activity. All the compounds tested in the desired concentrations did not show any significant absorbance at 620 nm under control conditions. Milrinone, a known PDE3 inhibitor drug has been used as a standard compound for comparison with the inhibitory activity of newly synthesized analogues. The concentration with 50% PDE3 activity ($IC_{50}$) of all tested compounds was calculated from dose response curves. $IC_{50}$ values of all compounds are summarized in Table 1.

TABLE 1

PDE3 inhibitory activity ($IC_{50}$) of Indolizinone derivatives.

| S. No | Compound Name | $IC_{50}$ (PDE3) |
|---|---|---|
| 1 | Milrinone | 3300 nM |
| 2 | 1a | 435.20 nM |
| 3 | 1c | 13.500 nM |
| 4 | 1d | 1600 nM |
| 5 | 1e | 129.10 nM |
| 6 | 1g | 108.02 nM |
| 7 | 1h | 576.80 nM |
| 8 | 1j | 11.300 nM |
| 9 | 1k | 67.300 nM |

SIGNIFICANCE OF THE WORK CARRIED OUT

The novel indolizinone based analogues have been synthesized, exhibited potent phosphodiesterase3 (PDE3) inhibition activity.

ADVANTAGES OF THE INVENTION

1. The present invention provides the synthesis of new indolizinone analogues useful as phosphodiesterase3 inhibitory agents.
2. The present invention provides a process for the preparation of novel indolizinone derivatives.
3. It is an another advantage that Baylis-Hillmanadducts used as synthons for the synthesis of targeted compounds.
4. It is an another advantage that the synthesized compounds are heterocyclic compound are heterocyclic derivatives.
5. It is an another advantage that the compounds are useful as cardiotonics.
6. It is an another advantage that bases utilised for the synthons are simple and base are commercially available.
7. It is an advantage that the method used for the synthesis of compounds is novel.

We claim:
1. A compound having formula 1

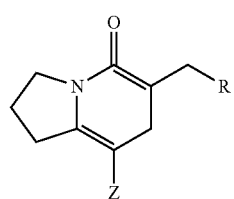

Formula 1 wherein Z = COOMe, COOEt

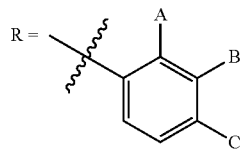

A = H, alkyl, alkoxy, halo,
B = H, alkyl, alkoxy, halo,
C = H, alkyl, alkoxy, halo.

2. The compound as claimed in claim 1, wherein the halogen is selected from the group consisting of fluorine, chlorine and bromine.

3. The compound as claimed in claim 1 wherein the representative compounds are:

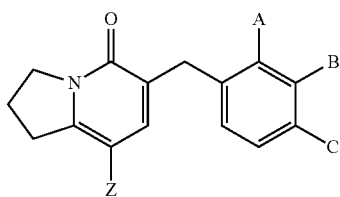

1a-p

Ethyl 6-benzyl-5-oxo-1,2,3,5-tetrahydroindolizinone-8-carboxylate, (1a)
Ethyl 6-(2-fluorobenzyl)-5-oxo-1,2,3,5-tetrahydroindolizinone-8-carboxylate, (1b)
Ethyl 6-(3-fluorobenzyl)-5-oxo-1,2,3,5-tetrahydroindolizinone-8-carboxylate, (1c)
Ethyl 6-(4-fluorobenzyl)-5-oxo-1,2,3,5-tetrahydroindolizinone-8-carboxylate, (1d)
Ethyl 6-(2-chlorobenzyl)-5-oxo-1,2,3,5-tetrahydroindolizinone-8-carboxylate, (1e)
Ethyl 6-(3-chlorobenzyl)-5-oxo-1,2,3,5-tetrahydroindolizinone-8-carboxylate, (1f)
Ethyl 6-(4-chlorobenzyl)-5-oxo-1,2,3,5-tetrahydroindolizinone-8-carboxylate, (1g)
Ethyl 6-(2,4-dichlorobenzyl)-5-oxo-1,2,3,5-tetrahydroindolizinone-8-carboxylate, (1h)
Ethyl 6-(2-bromobenzyl)-5-oxo-1,2,3,5-tetrahydroindolizinone-8-carboxylate, (1i)
Ethyl 6-(3-bromobenzyl)-5-oxo-1,2,3,5-tetrahydroindolizinone-8-carboxylate, (1j)
Ethyl 6-(4-bromobenzyl)-5-oxo-1,2,3,5-tetrahydroindolizinone-8-carboxylate, (1k)
Ethyl 5-oxo-6-(2-(trifluoromethyl)benzyl)-1,2,3,5-tetrahydroindolizinone-8-carboxylate, (1l)
Ethyl 5-oxo-6-(4-(trifluoromethyl)benzyl)-1,2,3,5-tetrahydroindolizinone-8-carboxylate, (1m)
Ethyl 6-(4-methylbenzyl)-5-oxo-1,2,3,5-tetrahydroindolizinone-8-carboxylate, (1n)
Ethyl 6-(4-ethylbenzyl)-5-oxo-1,2,3,5-tetrahydroindolizinone-8-carboxylate, (1o)
Ethyl 6-(4-isopropylbenzyl)-5-oxo-1,2,3,5-tetrahydroindolizinone-8-carboxylate (1p).

* * * * *